United States Patent
Schuch et al.

(10) Patent No.: US 9,890,107 B2
(45) Date of Patent: Feb. 13, 2018

(54) CROSS-LINKED POLYGLYCEROL ESTERS

(71) Applicant: Evonik Degussa GmbH, Essen (DE)

(72) Inventors: Dominik Schuch, Dusseldorf (DE); Christian Hartung, Essen (DE); Wolfgang Berkels, Bottrop (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/346,855

(22) Filed: Nov. 9, 2016

(65) Prior Publication Data

US 2017/0137366 A1 May 18, 2017

(30) Foreign Application Priority Data

Nov. 16, 2015 (EP) .................................. 15194652

(51) Int. Cl.
| | |
|---|---|
| *C07C 59/00* | (2006.01) |
| *C07C 69/40* | (2006.01) |
| *A61K 8/37* | (2006.01) |
| *A61Q 1/14* | (2006.01) |
| *A61Q 5/02* | (2006.01) |
| *A61Q 15/00* | (2006.01) |
| *A61Q 19/10* | (2006.01) |
| *C08G 63/668* | (2006.01) |
| *C08G 63/672* | (2006.01) |
| *A61K 8/39* | (2006.01) |
| *A61K 8/02* | (2006.01) |

(52) U.S. Cl.
CPC ............ *C07C 69/40* (2013.01); *A61K 8/0208* (2013.01); *A61K 8/375* (2013.01); *A61K 8/39* (2013.01); *A61Q 1/14* (2013.01); *A61Q 5/02* (2013.01); *A61Q 15/00* (2013.01); *A61Q 19/10* (2013.01); *C08G 63/668* (2013.01); *C08G 63/672* (2013.01); *A61K 2800/10* (2013.01); *A61K 2800/49* (2013.01)

(58) Field of Classification Search
CPC ....................................................... C07C 69/40
USPC ............................................................ 554/121
See application file for complete search history.

(56) References Cited

U.S. PATENT DOCUMENTS

| | | | |
|---|---|---|---|
| 6,242,499 | B1 | 6/2001 | Gruning et al. |
| 6,581,613 | B2 | 6/2003 | Berkels et al. |
| 7,635,581 | B2 | 12/2009 | Ferenz et al. |
| 7,851,511 | B2 | 12/2010 | Allef et al. |
| 7,855,265 | B2 | 12/2010 | Thum et al. |
| 7,906,664 | B2 | 3/2011 | Allef et al. |
| 8,198,473 | B2 | 6/2012 | Ferenz et al. |
| 8,211,972 | B2 | 7/2012 | Meyer et al. |
| 8,466,248 | B2 | 6/2013 | Meyer et al. |
| 8,685,376 | B2 | 4/2014 | Czech et al. |
| 8,729,207 | B2 | 5/2014 | Hartung et al. |
| 8,778,319 | B2 | 7/2014 | Herrwerth et al. |
| 8,841,400 | B2 | 9/2014 | Henning et al. |
| 8,993,792 | B2 | 3/2015 | Hartung et al. |
| 9,138,385 | B2 | 9/2015 | Dahl et al. |
| 9,271,908 | B2 | 3/2016 | Allef et al. |
| 9,320,697 | B2 | 4/2016 | Kleinen et al. |
| 9,409,853 | B2 | 8/2016 | Schuch et al. |
| 2006/0165627 | A1* | 7/2006 | Allef ............... A61K 8/39 424/70.11 |
| 2013/0071340 | A1 | 3/2013 | Wenk et al. |
| 2013/0259821 | A1 | 10/2013 | Henning et al. |
| 2013/0331592 | A1 | 12/2013 | Hartung et al. |
| 2014/0309446 | A1 | 10/2014 | Amajjahe et al. |
| 2015/0004112 | A1 | 1/2015 | Ritter et al. |
| 2015/0004113 | A1 | 1/2015 | Ritter et al. |
| 2015/0023900 | A1 | 1/2015 | Knott et al. |
| 2015/0297485 | A1 | 10/2015 | Klenin et al. |
| 2016/0081907 | A1 | 3/2016 | Schwab et al. |

FOREIGN PATENT DOCUMENTS

| | | |
|---|---|---|
| EP | 0835862 A1 | 4/1998 |
| EP | 1500427 A2 | 1/2005 |
| EP | 1683781 A2 | 7/2006 |
| WO | 2012007754 A1 | 1/2012 |

OTHER PUBLICATIONS

European Search Report dated May 9, 2016 in EP 15 19 4652 (6 pages).

\* cited by examiner

*Primary Examiner* — Deborah D Carr
(74) *Attorney, Agent, or Firm* — Philip P. McCann; Smith Moore Leatherwood LLP

(57) ABSTRACT

The invention provides polyglycerol partial esters based on mono- and dicarboxylic acids and their use as solubilizers, particularly in cosmetics, for example for perfume oils and essential oils in aqueous systems.

11 Claims, No Drawings

CROSS-LINKED POLYGLYCEROL ESTERS

This application claims the benefit of European Application No. 15194652.2 filed on Nov. 16, 2015, the disclosure of which is expressly incorporated herein by reference.

FIELD OF THE INVENTION

The invention provides polyglycerol partial esters based on mono- and dicarboxylic acids and their use as solubilizers, particularly in cosmetics, for example for perfume oils and essential oils in aqueous systems.

PRIOR ART

WO2012007754 discloses polyglycerol partial esters obtained by reacting polyglycerol having 3 to 20 glycerol units with a dicarboxylic acid or a cyclic anhydride of such a dicarboxylic acid having 4 to 22 carbon atoms and a monocarboxylic acid having 4 to 24 carbon atoms in a molar ratio of from 1.5:1.0:0.1 to 3.0:1.0:3.0, and also the use of these polyglycerol partial esters as emulsifier, solubilizer and/or thickener in body care and/or have care formulations.

EP0835862 describes polyglycerol partial esters of saturated or unsaturated, linear or branched fatty acids and polyfunctional carboxylic acids, obtainable by esterification of a polyglycerol mixture with saturated or unsaturated, linear or branched fatty acids having 12 to 22 carbon atoms and polyfunctional carboxylic acids having 4 to 54 carbon atoms and an average functionality of 2 to 2.4, wherein the degree of esterification of the polyglycerol mixture is from 30 to 75%.

EP1683781 describes polyglycerol partial esters of polyricinoleic acid and polyfunctional carboxylic acids, obtainable by esterification a) of a polyglycerol mixture with b) at least one particular polyricinoleic acid and optionally b1) polyhydroxystearic acid and c) at least one di- and/or tricarboxylic acid and d) at least one fatty acid according to methods known per se. The polyglycerol preferably has an average degree of condensation n of 1 to 11, preferably 2 to 6.

EP1500427 describes polyglycerol partial esters of polyhydroxystearic acid and polyfunctional carboxylic acids, obtainable by esterification of a polyglycerol mixture with polyhydroxystearic acid and di- and/or tricarboxylic acids and optionally/or with dimeric fatty acids and fatty acids having 6 to 22 carbon atoms.

A disadvantage of the polyglycerol partial esters described in the prior art is that these are not able to clearly solubilize relatively polar oils, with relatively low excesses of polyglycerol partial esters, in water or aqueous formulations. Relatively polar oils are, for example, essential oils and perfume oils, for example, rosemary or lemon oil. Polyglycerol esters having high proportions of dicarboxylic acids have a tendency that formulations for solubilizing oils are not clear and are opalescent.

A further disadvantage of the compounds described in the prior art is that these are not able to clearly solubilize perfume oils, with relatively low excesses of polyglycerol partial esters, in aluminium chlorohydrate-containing or other strongly electrolyte-containing formulations.

A further disadvantage of the compounds described in the prior art is that these are often relatively difficult to formulate, especially due to high viscosities of the products, or that difficult or lengthy formulation work is required during the preparation of the formulation.

SUMMARY

The object of the invention was to provide polyglycerol partial esters with which essential oils and perfume oils, using low amounts of polyglycerol partial esters, can be solubilized clearly and readily in water, in aqueous formulations, in aluminium chlorohydrate-containing or other strongly electrolyte-containing formulations.

DESCRIPTION OF THE INVENTION

Surprisingly, it has been found that the polyglycerol partial esters described below are able to solve the problem addressed by the invention.

The present invention therefore provides a polyglycerol partial ester obtainable by esterification of a polyglycerol with a carboxylic acid mixture comprising:
a) at least one short-chain dicarboxylic acid having 2 to 12, preferably 3 to 8, particularly preferably 4 carbon atoms, and
b) at least one saturated fatty acid having 6 to 14, preferably 8 to 10 carbon atoms, characterized in that the molar ratio of polyglycerol to dicarboxylic acid to saturated fatty acid is from 3.1:1.0:0.5 to 14:1.0:6.0, preferably from 3.3:1.0:0.7 to 7.0:1.0:3.0.

The invention further provides the use of corresponding polyglycerol partial esters as solubilizer.

An advantage of the present invention is that the polyglycerol partial esters described here are able to clearly solubilize hydrophobic, oil-soluble substances, such as essential oils, in water or in a cosmetic formulation.

A further advantage is that the polyglycerol partial esters described here may be prepared exclusively from renewable raw materials in contrast to polyethoxylated triglycerides (e.g. PEG-40 Hydrogenated Castor Oil).

Another advantage of the present invention is that formulations may be provided that are polyglycol ether-free.

A further advantage is that the polyglycerol partial esters described here are liquid, and thus readily processable, in contrast to polyethoxylated triglycerides. Also in comparison to polyglycerol esters of the prior art, the products according to the invention are comparatively easy to process. Owing to the comparatively low product viscosities, the fluidity can be further improved by low amounts of added solvents such as water or 1,2- and 1,3-propanediol or glycerol, in order to ensure even better processability.

A further advantage compared to the polyethoxylated triglycerides and even partly to the polyglycerol esters of the prior art is that the polyglycerol esters described here lead to obviously particularly clear dispersions of the oil in water, and also no cloudiness occurs on storage.

A further advantage of the polyglycerol partial esters described here is that these can produce a pleasant skin sensation in cosmetic formulations.

Another advantage of the polyglycerol partial esters described here is that these exhibit only a very low foam formation on stirring in water.

A further advantage is that the polyglycerol partial esters described here show only a very low effect on foamability and foam quantity in surfactant formulations, but the foam creaminess can, however, improve.

Another advantage is that the polyglycerol partial esters described here may lead to attenuation of skin irritancy in surfactant formulations.

Another advantage is that the polyglycerol partial esters described here may function as moisturizer (humectant) in cosmetic formulations.

A further advantage of the polyglycerol partial esters described here is that these can have a stabilizing effect in emulsions.

Another advantage of the products according to the invention is that these show particularly good results in make-up removers.

A further advantage of the products according to the invention is that these have a relatively low effect on the viscosity of surfactant formulations.

A further advantage of the products according to the invention is that these are relatively stable to oxidation and are stable with respect to color, odor and appearance.

Another advantage of the products according to the invention is that these are particularly compatible with electrolytes (such as sodium chloride, aluminium salts or cationic surfactants) in formulations.

The polyglycerol partial esters according to the invention are mixtures of different substances; it is therefore clear to those skilled in the art that the numeric values specified are average values for the mixture.

In the context of the present invention, the term "polyglycerol" is to be understood as meaning a polyglycerol which may also comprise glycerol. Consequently, for the purposes of calculating amounts, masses and the like, optionally a glycerol fraction should also be taken into consideration. Owing to its polymeric property, the polyglycerol is a statistical mixture of various compounds. Polyglycerol may have formed ether bonds between two primary, one primary and one secondary and also two secondary positions of the glycerol monomers. For this reason, the polyglycerol base skeleton does not usually consist exclusively of linearly linked glycerol units, but may also comprise branches and rings. For details see, e.g. "Original synthesis of linear, branched and cyclic oligoglycerol standards", Cassel et al., *J. Org. Chem.*, 2001, 875-896.

The same applies to the term "polyglycerol partial ester" in connection with the present invention.

Unless otherwise stated, all percentages (%) given are percentages by weight.

Preferred polyglycerol partial esters according to the invention are characterized in that the polyglycerol used has an average degree of condensation N of 1.5 to 9, preferably 2 to 7, particularly preferably 2.5 to 5.

The average degree of polymerization of the polyglycerol N is calculated via its hydroxyl number (OHN, in mg KOH/g) according to the following formula:

$$N = \frac{(112200 - 18 \cdot OHN)}{(74 \cdot OHN - 56100)}$$

Suitable methods for determining the hydroxyl number are particularly those according to DGF C-V 17 a (53), Ph. Eur. 2.5.3 Method A and DIN 53240.

A preferred polyglycerol partial ester according to the invention is therefore characterized in that the polyglycerol used has a hydroxyl number of 1500 to 900, preferably 1350 to 940, particularly preferably 1245 to 1010 mg KOH/g.

The polyglycerol used can be provided by different conventional methods such as, for example, polymerization of glycidol (e.g. base-catalysed), polymerization of epichlorohydrin (for example in the presence of equimolar amounts of a base such as NaOH) or polycondensation of glycerol.

The polyglycerol partial ester according to the invention is obtainable by esterification of a polyglycerol with a carboxylic acid mixture comprising components a) and b). It is preferred in accordance with the invention if components a) and b) make up in total at least 80% by weight, preferably at least 90% by weight, particularly preferably at least 95% by weight, based on the total carboxylic acid mixture used.

It is preferred in accordance with the invention if the dicarboxylic acid in the polyglycerol partial ester according to the invention is selected from aliphatic, linear dicarboxylic acids, in particular oxalic acid, malonic acid, tartronic acid, succinic acid, maleic acid, tartaric acid, malic acid, fumaric acid, sorbic acid, α-ketoglutaric acid, glutaric acid, adipic acid, pimelic acid, suberic acid, azelaic acid, sebacic acid, dodecanedioic acid, wherein succinic acid is particularly preferred.

A preferred polyglycerol partial ester according to the invention is characterized in that the saturated fatty acid is selected from unbranched, unsubstituted fatty acids.

A preferred polyglycerol partial ester according to the invention is characterized in that it has a saponification number of 70 to 199 mg KOH/g, preferably 95 to 190, particularly preferably 120 to 180 mg KOH/g. The determination of the saponification number is carried out by those skilled in the art according to DGF C-V 3 or DIN EN ISO 3681.

A preferred polyglycerol partial ester according to the invention is characterized in that in the esterification the molar ratio of a) to b) is
from 1.0:0.7 to 1.0:3.0, preferably
from 1.0:0.8 to 1.0:2.0, more preferably
from 1.0:1.0 to 1.0:1.6.

A preferred polyglycerol partial ester according to the invention is characterized in that at 1 bar it has a turbidity point of 45 to 75° C., preferably 50 to 65° C.

The turbidity point is determined according to DIN EN 1890. For this purpose, 0.9 g of polyglycerol partial ester is weighed out into a 250 ml glass beaker and 100 g of 10% NaCl solution are added. This composition is heated until a distinct cloudiness occurs. While stirring with a thermometer, the composition is allowed to cool until this is clear again; the temperature of the clarification is defined as the "turbidity point". This clear composition has a turbidity value of NTU<3. The cloudiness is measured with a HI88713 laboratory turbidity measuring instrument (ISO 7027, light detector: silicon photocell; light source: infrared LED) by the transmitted light method in the normal mode with respect to formazine and is stated in NTU.

A preferred polyglycerol partial ester according to the invention is characterized in that it has a viscosity of 20 to 200 Pa s, preferably 50 to 150 Pa s, at 25° C.

The viscosity is determined using a rheometer from Anton Paar, model MCR 301, parallel plate (40 mm) geometry at a temperature of 25° C. in the shear rate range of 0.1 $s^{-1}$ to 1000 $s^{-1}$. The value specified here of the viscosity is measured at a shear rate of 10 $s^{-1}$.

It is preferred in accordance with the invention if the polyglycerol partial ester according to the invention has an HLB value, according to Griffin, W. C.: Classification of surface active agents by HLB, J. Soc. Cosmet. Chem. 1, 1949, of 13 to 17.

The polyglycerol partial ester according to the invention preferably has a surface tension of less than 28 mN/m in 1.0% aqueous solution at 20° C.

The surface tension is measured in this case using a pendant drop tensiometer OCA 35 from Dataphysics Instruments (www.dataphysics.de). The value specified is the equilibrium value.

The polyglycerol partial esters of the present invention can be prepared by classical esterification methods; in place of carboxylic acids the corresponding carboxylic acid derivatives, their anhydrides or carboxylic esters for example (such as methyl or ethyl esters), may also of course be used.

The present invention further provides a composition comprising
the polyglycerol partial ester according to the invention and 10 to 50% by weight, preferably 20 to 40% by weight 1,2- or 1,3-propanediol
or
5% to 50% by weight, preferably 8% to 30% by weight water,
wherein the percentages by weight refer to the total composition and wherein the compositions have a viscosity of 0.1 to 10 Pa s, preferably 0.5 to 7.5 Pa s, at 25° C.

The present invention further relates to the use of at least one polyglycerol partial ester according to the invention as solubilizer, particularly of oils, particularly in cosmetic or pharmaceutical preparations.

The polyglycerol partial esters of the present invention are particularly used for solubilizing oils in water, aqueous and/or surfactant formulations. Likewise preferred is the use of at least one polyglycerol partial ester according to the invention as solubilizer of oils in aluminium chlorohydrate-containing cosmetic formulations, especially in deodorant formulations. The use according to the invention is applied particularly to polyether-free preparations. The examples adduced below illustrate the present invention by way of example, without any intention that the invention, the scope of application of which is apparent from the entirety of the description and the claims, be restricted to the embodiments specified in the examples.

EXAMPLES

Example 1: Inventive

Under a nitrogen atmosphere, 400 g of polyglycerol-3 (hydroxyl number=1155 mg KOH/g) were stirred with 80.0 g of caprylic/capric acid (0.30 mol equiv.) and 55.0 g of succinic acid (0.28 mol equiv.) at 240° C. until an acid number <1 mg KOH/g was achieved. The water formed during the course of the reaction was continuously distilled off After cooling to room temperature, the reaction product appeared as a pale yellow, clear to slightly cloudy liquid and had the following analytical data: viscosity: 120 Pa s; viscosity, 75% in 1,2-propanediol: 5.1 Pa s; acid number: 0.2 mg KOH/g; saponification number: 157 mg KOH/g; turbidity point: 56° C.

Example 2: Inventive

Under a nitrogen atmosphere, 400 g of polyglycerol-3 (hydroxyl number=1155 mg KOH/g) were stirred with 85.0 g of caprylic/capric acid (0.32 mol equiv.) and 55.0 g of succinic acid (0.28 mol equiv.) at 240° C. until an acid number <1 mg KOH/g was achieved. The water formed during the course of the reaction was continuously distilled off After cooling to room temperature, the reaction product appeared as a pale yellow, clear to slightly cloudy liquid and had the following analytical data: viscosity: 96 Pa s; acid number: 0.6 mg KOH/g; saponification number: 160 mg KOH/g; turbidity point: 52° C.

Example 3: Inventive

Under a nitrogen atmosphere, 400 g of polyglycerol-3 (hydroxyl number=1155 mg KOH/g) were stirred with 75.0 g of caprylic/capric acid (0.29 mol equiv.) and 40.0 g of succinic acid (0.20 mol equiv.) at 240° C. until an acid number <1 mg KOH/g was achieved. The water formed during the course of the reaction was continuously distilled off After cooling to room temperature, the reaction product appeared as a pale yellow, clear to slightly cloudy liquid and had the following analytical data: viscosity: 90 Pa s; acid number: 0.3 mg KOH/g; saponification number: 131 mg KOH/g; turbidity point: 50° C.

Example 4: Inventive

Under a nitrogen atmosphere, 500 g of polyglycerol-3 (hydroxyl number=1155 mg KOH/g) were stirred with 93.8 g of caprylic/capric acid (0.29 mol equiv.) and 25.0 g of succinic acid (0.10 mol equiv.) at 240° C. until an acid number <1 mg KOH/g was achieved. The water formed during the course of the reaction was continuously distilled off After cooling to room temperature, the reaction product appeared as a pale yellow, clear to slightly cloudy liquid and had the following analytical data: viscosity: 123 Pa s; acid number: 0.9 mg KOH/g; saponification number: 100 mg KOH/g; turbidity point: 69° C.

Example 5: Inventive

Under a nitrogen atmosphere, 300 g of polyglycerol-3 (hydroxyl number=1155 mg KOH/g) were stirred with 37.5 g of caprylic/capric acid (0.19 mol equiv.) at 180° C. for 11 h. After cooling to 50° C., 15.0 g of tartaric acid (0.08 mol equiv.) were added and the mixture was stirred at 180° C. for a further 14 h. The water formed during the course of the reaction was continuously distilled off. After cooling to room temperature, the reaction product appeared as a yellow, clear to slightly cloudy liquid and had the following analytical data: viscosity: 97 Pa s; acid number: 2.0 mg KOH/g; saponification number: 73 mg KOH/g; turbidity point: 51° C.

Example 6: Non-Inventive

Under a nitrogen atmosphere, 400 g of polyglycerol-3 (hydroxyl number=1155 mg KOH/g) were stirred with 85.0 g of caprylic/capric acid (0.32 mol equiv.) and 80.0 g of succinic acid (0.40 mol equiv.) at 240° C. until an acid number <1 mg KOH/g was achieved. The water formed during the course of the reaction was continuously distilled off After cooling to room temperature, the reaction product appeared as a pale yellow, clear to slightly cloudy liquid and had the following analytical data: viscosity: 297 Pa s; viscosity, 75% in 1,2-propanediol: 7.8 Pa s; acid number: 0.4 mg KOH/g; saponification number: 200 mg KOH/g; turbidity point: 56° C.

Example 7: Non-Inventive

Under a nitrogen atmosphere, 400 g of polyglycerol-3 (hydroxyl number=1155 mg KOH/g) were stirred with 85.0 g of caprylic/capric acid (0.32 mol equiv.) and 150 g of succinic acid (0.76 mol equiv.) at 240° C. until an acid number <1 mg KOH/g was achieved. The water formed during the course of the reaction was continuously distilled off. After cooling to room temperature, the reaction product appeared as a pale yellow, highly viscous, very sticky paste, such that most of the data were not determined due to the poor handling qualities: acid number: 0.8 mg; turbidity point: not measurable since product insoluble.

Example 8: TEGOSOFT® PC 41, Non-Inventive

Standard solubilizer, polyether-free. INCI: Polyglyceryl-4 Caprate. Commercial product of Evonik Nutrition & Care GmbH.

Example 9: NATRAGEM™ S 140, Non-Inventive

Solubilizer for oils, polyether-free. INCI: Polyglyceryl-4 Laurate/Sebacate (and) Polyglyceryl-6 Caprylate/Caprate (and) Aqua. Commercial product of Croda.

The products described above were tested in cosmetic formulations below.

The formulation constituents are named in the compositions in the form of the generally recognized INCI nomenclature using the English terms. All concentrations in the application examples are given in percentage by weight.

Example 10: ISOLAN GPS, Non-Inventive

W/O emulsifier, polyether-free. INCI: Polyglyceryl-4 Diisostearate/Polyhydroxystearate/Sebacate. Commercial product of Evonik Nutrition & Care GmbH.

Example 11: Non-Inventive

Under a nitrogen atmosphere, 67.6 g of polyglycerol-4 (hydroxyl number=1080 mg KOH/g) were stirred with 94.8 g of isostearic acid (1.55 mol equiv.) and 17.4 g of sebacic acid (0.40 mol equiv.) at 240° C. until an acid number of <10 mg KOH/g was achieved. 96.0 g of polyricinoleic acid (0.40 mol equiv., acid number=50 mg KOH/g) were then added and the mixture again stirred at 240° C. until an acid number of <5 mg KOH/g was achieved. The water formed during the course of the reaction was continuously distilled off After cooling to room temperature, the reaction product appeared as a yellow, clear to slightly cloudy liquid.

Example 12: Non-Inventive

Under a nitrogen atmosphere, 67.6 g of polyglycerol-4 (hydroxyl number=1080 mg KOH/g) were stirred with 104 g of isostearic acid (1.70 mol equiv.) and 17.4 g of sebacic acid (0.40 mol equiv.) at 240° C. until an acid number of <10 mg KOH/g was achieved. 90.0 g of polyricinoleic acid (0.37 mol equiv., acid number=50 mg KOH/g) and 22.0 g of polyhydroxystearic acid (0.09 mol equiv.) were then added and the mixture again stirred at 240° C. until an acid number of <5 mg KOH/g was achieved. The water formed during the course of the reaction was continuously distilled off. After cooling to room temperature, the reaction product appeared as a yellow, clear to slightly cloudy liquid.

Example 13: Non-Inventive

Under a nitrogen atmosphere, 175.8 g of polyglycerol-14 (hydroxyl number=850 mg KOH/g) were stirred with 88.4 g of isostearic acid (1.86 mol equiv.) and 22.5 g of sebacic acid (0.67 mol equiv.) at 240° C. until an acid number of <10 mg KOH/g was achieved. 157.5 g of polyhydroxystearic acid (0.76 mol equiv., acid number=45 mg KOH/g) were then added and the mixture again stirred at 240° C. until an acid number of <5 mg KOH/g was achieved. The water formed during the course of the reaction was continuously distilled off. After cooling to room temperature, the reaction product appeared as a yellow, clear to slightly cloudy, highly viscous liquid.

Example 14: Non-Inventive

Under a nitrogen atmosphere, 100 g of polyglycerol-4 (hydroxyl number=1080 mg KOH/g) were stirred with 88.4 g of isostearic acid (0.98 mol equiv.) and 157.5 g of polyhydroxystearic acid (0.41 mol equiv., acid number=47 mg KOH/g) at 240° C. until an acid number of <10 mg KOH/g was achieved. The mixture was then cooled to 130° C., 22.5 g of sebacic acid (0.35 mol equiv.) were added and the mixture again stirred at 240° C. until an acid number of <5 mg KOH/g was achieved. The water formed during the course of the reaction was continuously distilled off After cooling to room temperature, the reaction product appeared as a yellow, clear to slightly cloudy liquid.

Example 15: Non-Inventive

Under a nitrogen atmosphere, 61.9 g of polyglycerol-4 (hydroxyl number=1080 mg KOH/g) were stirred with 91.1 g of isostearic acid (1.62 mol equiv.) and 141.7 g of polyhydroxystearic acid (0.58 mol equiv., acid number=45 mg KOH/g) at 240° C. until an acid number of <10 mg KOH/g was achieved. The mixture was then cooled to 130° C., 14.6 g of adipic acid (0.51 mol equiv.) were added and the mixture again stirred at 240° C. until an acid number of <5 mg KOH/g was achieved. The water formed during the course of the reaction was continuously distilled off After cooling to room temperature, the reaction product appeared as a yellow, clear to slightly cloudy liquid.

Example 16: Comparison of Examples 1 to 4 with 6, 8 and 9 and 10 to 15 with Respect to Dissolving Power of Oils in Water In order to investigate the dissolving power of the inventive polyglycerol partial esters, these were mixed with cosmetic oils and treated with water. The oils tested were rosemary oil, lemon oil and the Spicy Herbs perfume oil (all from supplier Fragrance Resources). The proportion of solubilizer required to dissolve 0.5% of the respective oil completely clearly in water was investigated. Completely clear means that the solution has a turbidity value of NTU<3. To determine the dissolving power, the solubilizer (various amounts) was thoroughly mixed with the oil (0.5 g) and then slowly treated with water (made up to 100 g) with stirring. The mixture was stirred for half an hour at 25° C. A "clear mixture" must not become turbid again over a period of 3 days at 25° C.

In Table 1, the resulting mass ratios of solubilizer to oil which were required to obtain clear mixtures are summarized. It is also noted in the last column how readily the solubilizer could be formulated (+=easy processability, −=poor processability).

TABLE 1

Solubilizer-to-oil ratio required for a clear solution of the oil in water

|  | Lemon oil | Rosemary oil | Spicy Herbs | Processing at 20° C. |
|---|---|---|---|---|
| Polyglycerol partial ester Example 1 | 4:1 | 3:1 | 6:1 | + |
| Polyglycerol partial ester Example 2 | 4:1 | 3:1 | 6:1 | + |
| Polyglycerol partial ester Example 3 | 6:1 | 5:1 | 4:1 | + |
| Polyglycerol partial ester Example 4 | 8:1 | 4:1 | 7:1 | + |
| Polyglycerol partial ester Example 6 (non-inventive) | 9:1 | 4:1 | 7:1 | − |
| NATRAGEM ™ S 140 (Example 9, non-inventive) | 14:1 (opaque/not completely clear!) | 7:1 (opaque/not completely clear!) | 18:1 (opaque/not completely clear!) | + |
| TEGOSOFT ® PC 41 (Example 8, non-inventive) | 16:1 | 14:1 | 15:1 | ++ |
| ISOLAN ® GPS Example 10 (non-inventive) | >22:1 | >22:1 | >22:1 | + |
| Polyglycerol partial ester Example 11 (non-inventive) | >22:1 | >22:1 | >22:1 | + |
| Polyglycerol partial ester Example 12 (non-inventive) | >22:1 | >22:1 | >22:1 | + |
| Polyglycerol partial ester Example 13 (non-inventive) | >22:1 | >22:1 | >22:1 | − |
| Polyglycerol partial ester Example 14 (non-inventive) | >22:1 | >22:1 | >22:1 | + |
| Polyglycerol partial ester Example 15 (non-inventive) | >22:1 | >22:1 | >22:1 | + |

It is evident from the results in Table 1 that the inventive polyglycerol partial esters 1, 2, 3 and 4 almost always have better solubilizing properties than the Comparative Examples 6 and especially 8 and 9. Product 6 (with the high proportion of dicarboxylic acid in the polyglycerol ester), very similar to products 1-4, has a distinctly higher viscosity and, in addition to the somewhat poorer solubilization properties, is especially also significantly less processable than products 1-4. It is preferable to heat the mixture for processing of product 6 since otherwise the mixture with the oil is not uniformly well produced. Heating is not required for the other products. In the likewise very similar product 8 from the prior art it is also noticeable that it is not able to clearly dissolve the oils completely in water. The mixtures with product 8 are always somewhat opaque (even with considerably higher excesses of solubilizer than stated in the table above).

The non-inventive products 10 to 15 were neither able to solubilize the lemon oil or rosemary oil essential oils nor the Spicy Herbs perfume oil. Rather phase separation usually occurred in these experiments. These products are therefore not suitable for this application.

Example 17: Comparison of Example 2 to 8 and 9 with Respect to Dissolving Power of Oils in Aluminium Chlorohydrate-Containing Deodorant Roll-on Formulation In addition to the solution properties of the polyglycerol partial esters according to the invention for oils in water shown in Example 16, the dissolving power for oils was also investigated in a particularly demanding deodorant formulation (see Table 2) having a high aluminium chlorohydrate (ACH) content.

TABLE 2

Formulation Y for the assessment of the solubilization properties in a high aluminium chlorohydrate-containing deodorant formulation

| Phase | Ingredient | Proportion in % |
|---|---|---|
| A | Hydroxyethylcellulose, (Natrosol 250 HR, Ashland) | 1.00% |
|  | Water | to 100.00% |
| B | Aluminium chlorohydrate, 50% in water, (Locron L, Clariant) | 40.00% |
|  | Phenoxyethanol; methylisothiazolinone, (Neolone PE, preservative, Dow) | 0.45% |
| C | Fragrance oil (Spicy Herb or Pink Grapefruit, both from Fragrance Resources) | 1.00% |
|  | Solubilizer | q.s. |

For this purpose, the respective solubilizer was mixed with 1.0 g of the perfume oils Spicy Herb or Pink Grapefruit (both from Fragrance Resources) at room temperature for 5 min. In parallel, 1.0 g of hydroxyethylcellulose was added slowly to water at 45° C. with stirring and clearly dissolved over ca. 90-120 min with stirring (Phase A). Phase B with the aluminium chlorohydrate was then added with stirring to phase A. Finally, the mixture of phases A+B was added slowly with stirring to the mixture of solubilizer and perfume oil.

The proportion of solubilizer required to dissolve 1.0% of the perfume oil completely clearly in the deodorant system was investigated.

In Table 3, the resulting mass ratios of solubilizer-to-oil which were required to obtain clear mixtures are summarized.

TABLE 3

Solubilizer-to-oil ratio necessary for a clear solution of the respective perfume oil in the deodorant formulation Y

|  | Spicy Herbs | Pink Grapefruit |
|---|---|---|
| Polyglycerol partial ester Example 2 | 6:1 | 8:1 |
| NATRAGEM™ S 140 (Example 9, non-inventive) | >20:1 (phase separation overnight) | >20:1 (phase separation overnight) |
| TEGOSOFT® PC 41 (Example 8, non-inventive) | >20:1 | >20:1 |

The results in Table 3 show that the polyglycerol partial ester according to the invention of Example 2 has surprisingly very significantly improved solubilizer properties for the oils in this ACH formulation compared to the comparison products NATRAGEM™ S 140 and TEGOSOFT® PC 41. Even at a ratio of 20:1, the comparative examples are not able to clearly dissolve the oils in the formulation.

Example 18: Comparison of Example 1 to 6 and 9 with Respect to Skin Care Performance and Foam Properties To evaluate the skin care benefit and the foam properties of the inventive polyglycerol partial ester of Example 1 in aqueous surfactant formulations, a sensory handwashing test was conducted in comparison to the Comparative Examples 6 and 9 according to the prior art.

A group consisting of 10 trained test personnel washed their hands in a defined manner and assessed foam properties and skin feel using a grading scale from 1 (poor) to 5 (very good).

The products were formulated in each case in a standardized surfactant formulation, using the standard surfactant system of 9% active Sodium Laureth Sulfate and 3% active Cocamidopropyl Betaine (Table 4).

TABLE 4

Test formulation for the sensory handwashing test:

| | Formulation Example | | | |
|---|---|---|---|---|
| | U | V | W | X |
| Texapon® NSO-IS, 28%, (INCI: Sodium Laureth Sulfate, BASF) | 32.0% | 32.0% | 32.0% | 32.0% |
| TEGO® Betain F 50, 38%, (INCI: Cocamidopropyl Betaine, Evonik) | 8.0% | 8.0% | 8.0% | 8.0% |
| Sodium Chloride | 1.5% | 1.5% | 1.5% | 1.5% |
| Citric Acid | 0.2% | 0.2% | 0.2% | 0.2% |
| Water, demineralized | 58.3% | 55.3% | 55.3% | 54.55% |
| Polyglycerol partial ester Example 1 | — | 3.0% | — | — |
| Polyglycerol partial ester Example 6 (non-inventive) | — | — | 3.0% | — |
| NATRAGEM® S 140, 80% with 20% water, (Example 9, non-inventive) | — | — | — | 3.75% |

The sensory test results are summarized in Table 5.

TABLE 5

Results of the handwashing test:

| | Test formulation | | | |
|---|---|---|---|---|
| | U | V | W | X |
| Foaming behaviour | 3.3 | 3.6 | 3.6 | 3.5 |
| Foam volume | 3.0 | 3.1 | 3.1 | 3.1 |
| Foam creaminess | 2.7 | 3.9 | 3.9 | 4.0 |
| Skin feel during washing | 2.9 | 3.2 | 3.0 | 3.0 |
| Rinseability | 3.5 | 3.6 | 3.6 | 3.5 |
| Skin smoothness | 2.0 | 2.8 | 2.6 | 2.5 |
| Skin softness | 2.3 | 3.0 | 2.7 | 2.7 |
| Skin smoothness after 3 min | 3.0 | 3.6 | 3.3 | 3.2 |
| Skin softness after 3 min | 2.9 | 3.6 | 3.4 | 3.5 |

It is evident from the test results in Table 5 that the inventive formulation V using the inventive polyglycerol partial ester of Example 1 is superior, surprisingly, in skin smoothness and softness application properties in comparison to the comparative formulations W and X according to the prior art. Skin feel during washing is also best with formulation V. In this light, the results of the inventive formulation V can be designated as very good and show a distinct improvement compared to the prior art.

Example Formulations:

The formulation examples given in the tables below show exemplary representatives of a large number of possible compositions according to the invention.

If the preparation of the formulation requires the separate preparation or mixing of formulation constituents beforehand, this is termed multiphase preparation. If a two-phase preparation is required, the two phases are labelled A and B in the stated tables. In the case of three- or more-phase processes, the phases are called A, B, C etc. Unless stated otherwise, the data in the tables are data in % by weight. In the following formulation examples, the data or % by weight are based on the respective active substance. Some products, however, are commercially available as solutions, especially in water, such that in these cases more of the commercial products were used accordingly, depending on the active content.

"Product Example 1-9" correspond to "polyglycerol partial esters Example 1-9".

TABLE 6

Bath cream

| Water | to 100.0% |
|---|---|
| Sodium Laureth Sulfate | 8.0% |
| Coco-Glucoside | 4.0% |
| Cocamidopropyl Betaine | 4.0% |
| Product Example 2 | 1.5% |
| PEG-18 Glyceryl Oleate/Cocoate | 2.0% |
| Perfume Spicy Herbs | 0.2% |

TABLE 6-continued

Bath cream

| | |
|---|---|
| Polyglyceryl-4 Caprate | 0.5% |
| *Citrus Aurantifolia* (Lime) Oil | 0.2% |
| Linalool | 0.1% |
| Coumarin | 0.1% |
| Glycerol | 0.5% |
| Glycol Distearate | 0.5% |
| Styrene/Acrylates Copolymer | 0.2% |
| Tocopherol | 0.1% |
| Preservative | q.s. |
| Citric Acid | to pH 5.2 |

TABLE 7

Shower cream

| | |
|---|---|
| Water | to 100.0% |
| Glycerol | 4.0% |
| Sodium Laureth Sulfate | 4.0% |
| Cocamidopropyl Betaine | 3.5% |
| Product Example 3 | 1.8% |
| Coco-Glucoside | 1.8% |
| *Ricinus Communis* Seed Oil (seed) | 0.2% |
| Glyceryl Oleate | 0.5% |
| Polyglyceryl-6 Caprylate; Polyglyceryl-3 Cocoate; Polyglyceryl-4 Caprate; Polyglyceryl-6 Ricinoleate | 1.0% |
| *Argania Spinosa* Kernel Oil | 0.1% |
| *Butyrospermum Parkii* Butter Extract | 0.1% |
| Limonene | 0.1% |
| Perfume | 0.2% |
| Acrylates/C10-30 Alkyl Acrylate Crosspolymer | 0.2% |
| Hydroxypropyl Methylcellulose | 0.2% |
| Styrene/Acrylates Copolymer | 0.2% |
| Sodium Hydroxide | 0.2% |
| Glycol Distearate | 0.4% |
| Silica | 0.2% |
| Tocopherol | 0.1% |
| Preservative | q.s. |
| Citric acid | to pH 5.2 |

TABLE 8

Bath oil

| | |
|---|---|
| Water | to 100.0% |
| Sodium Laureth Sulfate | 6.0% |
| Cocamidopropyl Betaine | 6.0% |
| Cocamide DEA | 2.5% |
| Sodium Trideceth Sulfate | 2.2% |
| Product Example 2 | 1.0% |
| Perfume | 0.5% |
| PEG-40 Hydrogenated Castor Oil | 0.2% |
| Trideceth-9 | 0.2% |
| Sodium Lauroamphoacetate | 0.5% |
| Benzophenone-4 | 0.2% |
| Cocamide MEA | 0.4% |
| Propylene Glycol | 0.5% |
| Disodium EDTA | 0.1% |
| Sodium Chloride | 0.6% |
| Glycerol | 0.5% |
| Benzyl Alcohol | 0.4% |
| Sodium Cocoyl Glutamate | 0.4% |
| Phenoxyethanol | 0.2% |
| Xanthan Gum | 0.2% |
| Carbomer | 0.2% |
| Lactic Acid | 0.3% |
| Magnesium Chloride | 0.1% |
| Coumarin | 0.1% |
| Citric Acid | to pH 5.2 |
| Preservative | q.s. |

TABLE 9

Shower cream

| | |
|---|---|
| Water | to 100.0% |
| Sodium Laureth Sulfate | 8.0% |
| Glycerol | 2.5% |
| Cocamidopropyl Betaine | 2.5% |
| Product Example 3 | 2.0% |
| Decyl Glucoside | 1.5% |
| Perfume | q.s. |
| Sodium Chloride | 1.5% |
| PEG-40 Hydrogenated Castor Oil | 0.5% |
| *Glycine Soja* Oil | 0.1% |
| *Helianthus Annuus* Seed Oil | 0.1% |
| Lecithin | 0.2% |
| Coco-Glucoside | 0.5% |
| Glyceryl Oleate | 0.2% |
| Coumarin | 0.1% |
| Preservative | q.s. |

TABLE 10

Body shampoo

| | | |
|---|---|---|
| Phase A | Product Example 2 | 3.0% |
| | *Salvia Officinalis* (Sage) Oil | 0.3% |
| | Perfume | 0.1% |
| Phase B | Sodium Cocoamphoacetate | 3.5% |
| Phase C | Water | to 100.0% |
| | Acrylates/C10-30 Alkyl Acrylate Crosspolymer | 0.9% |
| Phase D | Sodium Lauroyl Methyl Isethionate | 5.0% |
| | Capryl/Capramidopropyl Betaine | 1.5% |
| | Citric Acid | 1.2% |
| Phase E | Water | 10.0% |
| | Polyquaternium-7 | 0.3% |
| | Preservative | q.s. |

TABLE 11

Body shampoo

| | | |
|---|---|---|
| Phase A | Product Example 1 | 4.0% |
| | *Lavandula Angustifolia* (Lavender) Oil | 0.2% |
| | Perfume | 0.2% |
| Phase B | Water | to 100.0% |
| Phase C | Sodium Cocoamphoacetate | 4.0% |
| Phase D | Water | 30.0% |
| | Acrylates/Beheneth-25 Methacrylate Copolymer | 1.7% |
| | Sodium Lauroyl Methyl Isethionate | 4.0% |
| | Disodium Lauryl Sulfosuccinate | 1.7% |
| Phase E | Preservative | q.s. |

TABLE 12

Shampoo

| | | |
|---|---|---|
| Phase A | Product Example 2 | 3.0% |
| | Orange Oil | 0.3% |
| | Perfume | 0.1% |
| Phase B | Water | to 100.0% |
| Phase C | Disodium Cocoamphodiacetate | 5.0% |
| Phase D | Glycerol | 1.0% |
| | Xanthan Gum | 0.7% |
| | Water | 25.0% |
| Phase E | Water | 10.0% |
| | Acrylates/Beheneth-25 Methacrylate Copolymer | 2.0% |
| Phase F | Water | 10.0% |
| | Polyquaternium-10 | 0.3% |
| Phase G | Cocamidopropyl Betaine | 5.0% |
| | Preservative | q.s. |

TABLE 13

Shampoo

| Phase | Ingredient | Amount |
|---|---|---|
| Phase A | Product Example 2 | 5.0% |
| | Lemongrass Oil | 0.5% |
| Phase B | Water | to 100.0% |
| Phase C | Perfume | 0.2% |
| | Polyglyceryl-4 Caprate | 2.0% |
| Phase D | Water | 20.0% |
| Phase E | Sodium Laureth Sulfate | 8.0% |
| Phase F | Water | 10.0% |
| | Cocamidopropyl Betaine | 4.0% |
| | PEG-120 Methyl Glucose Dioleate | 1.2% |
| Phase G | Water | 10.0% |
| | Sodium Chloride | 0.9% |
| | Polyquaternium-10 | 0.2% |
| Phase H | Citric Acid | to pH 5.5 |
| Phase I | Preservative | q.s. |

TABLE 14

Shower gel

| Phase | Ingredient | Amount |
|---|---|---|
| Phase A | Product Example 2 | 3.0% |
| | *Mentha Piperita* (Peppermint) Oil | 0.2% |
| | Rosemary Oil | 0.2% |
| | Perfume | 0.1% |
| Phase B | Water | to 100.0% |
| Phase C | Sodium Cocoamphoacetate | 5.5% |
| Phase D | Lauryl Glucoside | 4.5% |
| Phase E | Coco-Glucoside | 1.3% |
| Phase F | Sodium/Disodium Cocoyl Glutamate | 3.5% |
| | Water | 10.0% |
| | Glycerol | 0.8% |
| Phase G | Water | 10.0% |
| | Xanthan Gum | 2.2% |
| Phase H | Citric acid | to pH 6.0 |
| Phase I | Preservative | q.s. |

TABLE 15

Shampoo

| Phase | Ingredient | Amount |
|---|---|---|
| Phase A | Product Example 1 | 4.0% |
| | Isopropyl Myristate | 0.2% |
| | Perfume | 0.1% |
| Phase B | Water | to 100.0% |
| Phase C | Sodium Lauryl Sulfate | 9.0% |
| Phase D | Cocamidopropyl Betaine | 3.0% |
| Phase E | Cocamide MEA | 2.0% |
| | Xanthan Gum | 0.2% |
| | Water | 10.0% |
| Phase F | Water | 10.0% |
| | Polyquaternium-10 | 0.2% |
| Phase G | Citric acid | to pH 5.5 |
| Phase H | Preservative | q.s. |

TABLE 16

Cleansing Oil Shampoo

| Ingredient | Amount |
|---|---|
| Water | to 100.0% |
| Sodium Laureth Sulfate | 6.0% |
| MIPA-Laureth sulfate | 3.0% |
| Sodium Chloride | 2.5% |
| Cocamidopropyl Betaine | 2.5% |
| Polyglyceryl-6 Caprylate; Polyglyceryl-3 Cocoate; Polyglyceryl-4 Caprate; Polyglyceryl-6 Ricinoleate | 2.5% |
| Glycerol | 2.5% |
| PEG-18 Castor Oil Dioleate | 2.0% |
| Propylene Glycol; PEG-55 Propylene Glycol Oleate | 2.0% |
| Product Example 2 | 2.0% |
| Laureth-5 Carboxylic Acid | 1.0% |
| *Persea Gratissima* (Avocado) Oil | 0.5% |
| Sodium benzoate | 0.7% |
| Salicylic Acid | 0.3% |
| Linalool | 0.2% |
| alpha-Isomethyl Ionone | 0.1% |
| Limonene | 0.1% |
| *Camellia Oleifera* Seed Oil | 0.1% |
| Citric Acid | to pH 5.0 |
| Perfume, Dyes | q.s. |

TABLE 17

Shower Cream

| Ingredient | Amount |
|---|---|
| Water | to 100% |
| Glycerol | 7.0% |
| *Glycine Soya* Oil | 3.0% |
| Lauryl Glucoside | 3.0% |
| Sodium Coco-Sulfate | 3.0% |
| Product Example 2 | 2.5% |
| Alcohol | 1.5% |
| Xanthan Gum | 1.5% |
| *Butyrospermum Parkii* Butter Extract | 1.0% |
| Sodium Cetearyl Sulfate | 1.0% |
| Sodium Cocoyl Glutamate | 1.0% |
| Disodium Cocoyl Glutamate | 1.0% |
| Tocopherol | 0.1% |
| *Helianthus Annuus* Seed Oil | 0.3% |
| Limonene | 0.1% |
| Benzyl Salicylate | 0.1% |
| Linalool | 0.1% |
| Dyes | q.s. |

TABLE 18

Shower Gel

| Ingredient | Amount |
|---|---|
| Water | to 100% |
| Sodium Coco-Sulfate | 5.0% |
| Glycerol | 4.0% |
| Lauryl Glucoside | 4.0% |
| Sodium Lactate | 2.5% |
| Product Example 3 | 2.0% |
| Polyglyceryl-4 Caprate | 2.0% |
| Sodium Cocoyl Glutamate | 2.0% |
| Disodium Cocoyl Glutamate | 1.0% |
| Alcohol | 1.0% |
| *Prunus Cerasus* Fruit Extract | 1.0% |
| Limonene | 0.1% |
| Coumarin | 0.2% |
| Linalool | 0.1% |
| Citral | 0.1% |
| Dyes | q.s. |

TABLE 19

Liquid Soap

| Ingredient | Amount |
|---|---|
| Water | to 100% |
| Glycerol | 4.0% |
| Alcohol | 4.0% |
| Sodium Coco-Sulfate | 3.0% |
| Lauryl Glucoside | 3.0% |
| Product Example 1 | 2.0% |
| Xanthan Gum | 1.5% |
| *Mangifera Indica* (Mango) Fruit Extract | 0.5% |
| Limonene | 0.1% |
| Linalool | 0.1% |
| Dyes | q.s. |

TABLE 20

| Shampoo for Children | |
| --- | --- |
| Water | to 100% |
| Sodium Coco Sulfate | 7.0% |
| Decyl Glucoside | 4.0% |
| Lactis Proteinum | 2.5% |
| Sorbitan Caprylate | 2.0% |
| Product Example 2 | 2.0% |
| Glycerol | 2.0% |
| Sodium Lactate | 2.0% |
| Alcohol | 2.0% |
| Hydrolyzed Wheat Protein | 0.3% |
| Hydrolyzed Wheat Starch | 0.3% |
| Sodium Chloride | 0.9% |
| Limonene | 0.1% |
| Citral | 0.1% |
| Phenethyl Alcohol | 0.1% |
| Dyes | q.s. |

TABLE 21

| Cream Soap | |
| --- | --- |
| Water | to 100% |
| Alcohol | 7.0% |
| Coco-Glucoside | 5.0% |
| Glycerol | 5.0% |
| Product Example 1 | 2.5% |
| Disodium Cocoyl Glutamate | 2.5% |
| Xanthan Gum | 1.5% |
| Citric Acid | to pH 5.5 |
| *Malva Sylvestris* Leaf Extract | 1.0% |
| Glyceryl Oleate | 1.0% |
| Sodium Cocoyl Glutamate | 0.8% |
| Linalool | 0.1% |
| Limonene | 0.1% |
| Dyes | q.s. |

TABLE 22

| Shower Crème | |
| --- | --- |
| Water | to 100% |
| Ammonium Lauryl Sulfate | 11.0% |
| Product Example 2 | 3.5% |
| *Aloe Barbadensis* Leaf Juice | 1.5% |
| Cocamidopropyl Betaine | 1.5% |
| Decyl Glucoside | 1.5% |
| Glycerol | 1.0% |
| *Prunus Amygdalus Dulcis* (Sweet Almond) Oil | 0.4% |
| Glyceryl Oleate | 0.2% |
| Lauryl Glucoside | 0.3% |
| Coco-Glucoside | 0.4% |
| Benzyl Alcohol | 0.2% |
| Benzoic Acid | 0.2% |
| Dehydroacetic Acid | 0.1% |
| Sodium Benzoate | 0.3% |
| Potassium Sorbate | 0.2% |
| Tocopherol | 0.1% |
| Citric Acid | to pH 4.9 |
| Perfume, Dyes | q.s. |

TABLE 23

| Shower Crème | |
| --- | --- |
| Water | to 100% |
| Sodium Laureth Sulfate | 9.0% |
| Product Example 2 | 3.0% |
| Cocamidopropyl Betaine | 3.0% |
| Glycerol | 1.0% |
| Glucose | 0.5% |
| *Prunus Amygdalus Dulcis* (Sweet Almond) Oil | 0.5% |

TABLE 23-continued

| Shower Crème | |
| --- | --- |
| Sodium Chloride | 0.5% |
| Polyquaternium-7 | 0.3% |
| Styrene/Acrylates Copolymer | 0.3% |
| PEG-200 Hydrogenated Glyceryl Palmate; PEG-7 Glyceryl cocoate | 0.6% |
| Citric Acid | to pH 5.5 |
| Perfume, Dyes | q.s. |

TABLE 24

| Care shower | |
| --- | --- |
| Water | to 100% |
| Sodium Laureth Sulfate | 9.5% |
| Sodium Hydroxypropyl Starch Phosphate | 2.5% |
| Product Example 2 | 2.0% |
| Cocamidopropyl Betaine | 2.5% |
| Petrolatum | 0.4% |
| Sodium Cocoyl Glycinate | 0.9% |
| Lauric Acid | 0.5% |
| Sodium Lauroyl Isethionate | 0.7% |
| Glycerol | 0.5% |
| *Helianthus Annuus* Seed Oil | 0.2% |
| *Olea Europaea* Fruit Oil | 0.1% |
| Sodium Chloride | 0.5% |
| Stearic Acid | 0.3% |
| Guar Hydroxypropyltrimonium Chloride | 0.3% |
| Sodium Isethionate | 0.1% |
| Tetrasodium EDTA | 0.1% |
| Alumina | 0.1% |
| Citric Acid | to pH 5.5 |
| Perfumes, Dyes, Preservatives | q.s. |

TABLE 25

| Shower Crème | |
| --- | --- |
| Water | to 100% |
| Sodium Coco-Sulfate | 15.0% |
| Glycerol | 3.5% |
| Product Example 3 | 3.5% |
| *Glycine Soja* Oil | 0.3% |
| Coco-Glucoside | 0.9% |
| Caprylic/Capric Triglyceride | 0.1% |
| Xanthan Gum | 0.8% |
| *Prunus Amygdalus Dulcis* Oil | 0.1% |
| Sodium Cocoyl Glutamate | 0.3% |
| Disodium Cocoyl Glutamate | 0.5% |
| Sodium Cetearyl Sulfate | 0.2% |
| Tocopherol | 0.1% |
| *Helianthus Annuus* Seed Oil | 0.1% |
| Alcohol | 0.8% |
| Citral | 0.1% |
| Geraniol | 0.1% |
| Limonene | 0.1% |
| Linalool | 0.1% |
| Citric Acid | to pH 5.3 |
| Perfume, Dyes | q.s. |

TABLE 26

| Pampering Oil Bath | |
| --- | --- |
| Water | to 100.0% |
| *Glycine Soya* Oil | 20.0% |
| Product Example 1 | 10.0% |
| Polyglyceryl-3 Palmitate | 4.5% |
| Glyceryl Caprylate | 4.5% |
| *Simmondsia Chinensis* Seed Oil | 1.5% |
| *Prunus Amygdalus Dulcis* (Sweet Almond) Oil | 1.0% |
| *Triticum Vulgare* Germ Oil | 1.0% |

TABLE 26-continued

Pampering Oil Bath

| | |
|---|---|
| Tocopherol | 0.2% |
| Limonene | 0.1% |
| Citral | 0.1% |
| Dyes | q.s. |

TABLE 27

Deo

| Phase | Ingredient | % |
|---|---|---|
| Phase A | Product Example 2 | 3.0% |
| | Isopropyl Palmitate | 0.1% |
| | Rosemary Oil | 0.1% |
| | Perfume | 0.1% |
| Phase B | Phenoxyethanol | 0.5% |
| | Caprylyl Glycol | 0.2% |
| Phase C | Water | 50.0% |
| | Hydroxyethyl Cellulose | 0.7% |
| | Sodium Hydroxide (10% in water) | 0.2% |
| Phase D | Aluminium Chlorohydrate | 19.0% |
| Phase E | Water | to 100.0% |

TABLE 28

Deo

| Phase | Ingredient | % |
|---|---|---|
| Phase A | Phenoxyethanol | 0.5% |
| | Methylisothiazolinone | 0.001% |
| | Aluminium Chlorohydrate | 20.0% |
| Phase B | Hydroxyethyl Cellulose | 1.0% |
| | Water | to 100.0% |
| Phase C | Product Example 3 | 1.5% |
| | Perfume Spicy Herbs | 0.3% |

TABLE 29

Deo

| Phase | Ingredient | % |
|---|---|---|
| Phase A | Product Example 1 | 2.0% |
| | Perfume Pink Grapefruit | 0.2% |
| Phase B | Phenoxyethanol | 0.5% |
| | Caprylyl Glycol | 0.2% |
| Phase C | Water | 50.0% |
| | Hydroxyethyl Cellulose | 0.75% |
| | Sodium Hydroxide (10% in water) | 0.25% |
| Phase D | Aluminium Chlorohydrate | 10.0% |
| Phase E | Water | to 100.0% |

TABLE 30

Antitranspirant Deo Roll-On

| Phase | Ingredient | % |
|---|---|---|
| Phase A | Polyglyceryl-6 Caprylate; Polyglyceryl-3 Cocoate; Polyglyceryl-4 Caprate; Polyglyceryl-6 Ricinoleate | 4.0% |
| | Decyl Oleate | 0.1% |
| | *Aloe Barbadensis* Leaf Extract | 0.1% |
| | *Glycine Soya* Oil | 0.1% |
| Phase B | Product Example 1 | 2.8% |
| | Perfume | 0.1% |
| | Distearyl Ether | 0.3% |
| | Stearyl Alcohol | 0.1% |
| Phase C | Aluminium Chlorohydrate | 10.0% |
| | Water | to 100.0% |
| Phase D | Phenoxyethanol | 0.6% |
| | Ethylhexylglycerin | 0.2% |

TABLE 31

Anti-Transpirant Deo

| Phase | Ingredient | % |
|---|---|---|
| Phase A | Product Example 2 | 3.5% |
| | Dicaprylyl Ether | 0.2% |
| | Geraniol | 0.1% |
| | Linalool | 0.1% |
| | Perfume Spicy Herbs | 0.1% |
| Phase B | Propylene Glycol | 1.0% |
| | Butylene Glycol | 0.5% |
| | Water | 5.0% |
| | Palmitamidopropyltrimonium Chloride | 1.5% |
| Phase C | Water | 50.0% |
| | Hydroxyethyl Cellulose | 0.8% |
| | Sodium Hydroxide (10% in water) | 0.3% |
| Phase D | Aluminium Chlorohydrate | 15.0% |
| Phase E | Water | to 100.0% |

TABLE 32

Deo

| Phase | Ingredient | % |
|---|---|---|
| Phase A | Product Example 1 | 2.8% |
| | Dicaprylyl Ether | 0.2% |
| | Isoceteth-20 | 0.5% |
| | Geraniol | 0.1% |
| | Allantoin | 0.1% |
| | Linalool | 0.1% |
| | Limonene | 0.1% |
| | Butylene Glycol | 0.8% |
| | Perfume Pink Grapefruit | 0.1% |
| Phase B | Propylene Glycol | 1.0% |
| | Water | 5.0% |
| | Palmitamidopropyltrimonium Chloride | 1.5% |
| Phase C | Water | 50.0% |
| | Glyceryl Isostearate | 0.5% |
| | PEG-150 Distearate | 0.3% |
| Phase D | Aluminium Chlorohydrate | 10.0% |
| Phase E | Water | to 100.0% |

TABLE 33

Formulation for Wet Wipes

| | |
|---|---|
| Butylene Glycol | 1.0% |
| Glycerol | 1.0% |
| Product Example 1 | 1.5% |
| Silicone Quaternium-22; Polyglycerol-3 Caprate; Dipropylene Glycol; Cocamidopropyl Betaine | 0.5% |
| Allantoin | 0.2% |
| Maltodextrin | 0.5% |
| *Chamomilla Recutita* Extract | 0.1% |
| Phenoxyethanol; Ethylhexylglycerol | 0.7% |
| Perfume | q.s. |
| Water | to 100.0% |
| Citric Acid, 30% | to pH 5.5 |

TABLE 34

Solution for Wet Wipes

| | |
|---|---|
| Product Example 2 | 1.5% |
| Perfume | 0.2% |
| Glycerol | 2.0% |
| Sodium Lactate; Sodium PCA; Glycine; Fructose; Urea; Niacinamide; Inositol; Sodium Benzoate; Lactic Acid | 0.1% |
| Water | to 100.0% |
| Preservative | q.s. |

TABLE 35

Solution for Wet Wipes

| | |
|---|---|
| Product Example 3 | 3.0% |
| Polyglyceryl-4 Caprate | 2.0% |
| Isopropyl myristate | 0.3% |
| Phenoxyethanol; Methylparaben; Ethylparaben; Butylparaben; Propylparaben; Isobutylparaben | 0.2% |
| Perfume | 0.1% |
| Propylene Glycol | 2.0% |
| Water | to 100.0% |
| Cetrimonium bromide | 0.1% |

TABLE 36

Solution for Wet Wipes

| | |
|---|---|
| Product Example 2 | 3.0% |
| *Aloe barbadensis* leaf extract | 0.3% |
| Disodium Cocoamphodiacetate | 0.5% |
| Perfume | 0.2% |
| Propylene Glycol | 2.5% |
| Hydrolyzed Silk | 0.1% |
| Caprylyl/Capryl Glucoside | 1.0% |
| Water | to 100.0% |
| Phenoxyethanol | 0.5% |
| Dehydroacetic Acid | 0.1% |
| Benzoic Acid | 0.1% |
| Sodium Benzoate | 0.4% |

TABLE 37

Make-up Remover

| | |
|---|---|
| Sodium Cocoamphopropionate | 5.0% |
| Propylene Glycol | 35.0% |
| Product Example 1 | 30.0% |
| Glycerol | 30.0% |
| Preservative | q.s. |

TABLE 38

Make-up Remover

| | |
|---|---|
| Cocamidopropyl Betaine | 7.0% |
| Water | to 100.0% |
| Product Example 2 | 4.0% |
| Glycerol | 8.0% |
| Citric Acid | to pH 5.5 |
| Preservative | q.s. |

TABLE 39

Make-up Remover

| | |
|---|---|
| Capryl/Capramidopropyl Betaine | 2.0% |
| Water | to 100.0% |
| Product Example 2 | 3.0% |
| Glycerol | 3.0% |
| Citric Acid | to pH 5.5 |
| Preservative | q.s. |

TABLE 40

Make-up Remover

| | |
|---|---|
| Polyglyceryl-4 Caprate | 1.0% |
| Water | to 100.0% |
| Product Example 2 | 1.5% |

TABLE 40-continued

Make-up Remover

| | |
|---|---|
| Polyglyceryl-6 Caprylate; Polyglyceryl-3 Cocoate; Polyglyceryl-4 Caprate; Polyglyceryl-6 Ricinoleate | 1.2% |
| Propylene Glycol | 1.0% |
| Glycerol | 2.5% |
| Citric Acid | to pH 5.5 |
| Preservative | q.s. |

TABLE 41

O/W Make-up remover wipe

| | | |
|---|---|---|
| Phase A | Ethylhexyl Stearate; Phenoxyethanol; Polyglyceryl-4 Laurate; Sorbitan Laurate; Dilauryl Citrate | 4.0% |
| | Cetyl Ricinoleate | 0.8% |
| Phase B | Water | to 100.0% |
| | Glycerol | 1.5% |
| Phase C | Product Example 3 | 1.0% |
| Phase D | Phenoxyethanol | 0.2% |
| | Perfume | q.s. |
| | Preservative | q.s. |

TABLE 42

Micellar water

| | |
|---|---|
| Water | to 100.0% |
| Product Example 2 | 4.0% |
| Glycerol | 1.5% |
| Disodium Cocoamphodiacetate | 0.5% |
| Disodium EDTA | 0.2% |
| Polyaminopropyl Biguanide | 0.2% |
| Citric Acid, 30% | to pH 5.5 |

TABLE 43

Micellar Solution Cleanser

| | |
|---|---|
| Water | to 100.0% |
| Butylene Glycol | 5.0% |
| Coco-Glucoside | 2.0% |
| Product Example 2 | 2.5% |
| Glycerol | 1.0% |
| Allantoin | 0.1% |
| *Curcuma Longa* (Turmeric) Root Extract | 0.2% |
| Perfume | 0.2% |
| Citric Acid, 30% | to pH 5.5 |

TABLE 44

Cleansing Water

| | |
|---|---|
| Water | to 100.0% |
| Product Example 1 | 2.5% |
| Phenoxyethanol; Ethylhexylglycerol | 0.9% |
| Perfume Pink Grapefruit | 0.2% |
| Glycerol | 0.5% |
| Disodium EDTA | 0.2% |
| Citric Acid, 30% | to pH 5.5 |

TABLE 45

Micellar water

| | |
|---|---|
| Water | to 100.0% |
| Product Example 2 | 3.0% |
| Glycerol | 1.0% |

TABLE 45-continued

| Micellar water | | |
|---|---|---|
| Capryl/Capramidopropyl Betaine | 1.5% | |
| Disodium EDTA | 0.2% | |
| Perfume Pink Grapefruit | 0.2% | |
| Citric Acid, 30% | to pH 5.5 | |

TABLE 46

Further formulation examples

| | 46a | 46b | 46c | 46d | 46e | 46f | 46g | 46h | 46i | 46j |
|---|---|---|---|---|---|---|---|---|---|---|
| Water | to 100% | | | | | | | | | |
| Product Example 1 | 2.5% | 3.5% | 3.5% | 1.0% | 3.0% | 2.5% | 5.0% | 3.0% | 3.5% | 3.5% |
| Sodium Laureth Sulfate | 9.0% | 8.0% | 9.0% | — | — | — | — | — | — | — |
| Sodium Lauryl Sulfate | — | — | — | 6.0% | — | — | — | — | 3.5% | — |
| Cocamidopropyl Betaine | — | 2.0% | 3.0% | 5.0% | 5.0% | 6.0% | — | — | 2.0% | 7.5% |
| Sodium Cocoamphoacetate | 3.0% | — | — | 1.5% | 4.5% | — | 3.5% | — | 3.5% | — |
| Lauryl Glucoside | — | — | — | — | 3.5% | 5.0% | 3.0% | 7.0% | — | — |
| Coco-Glucoside | — | 1.5% | — | — | 1.5% | 1.0% | 5.0% | 2.5% | 2.0% | — |
| Sodium Cocoyl Glutamate | — | — | — | — | — | 1.0% | 1.7% | 5.0% | 0.5% | — |
| Stearic Acid | — | — | — | — | — | — | — | — | 0.1% | 3.5% |
| Sucrose Cocoate | 0.5% | — | 1.0% | 1.2% | 0.3% | 0.2% | — | 1.0% | 1.0% | 1.0% |
| Glycerol | 0.5% | 1.0% | 0.5% | — | 0.3% | 0.5% | 1.5% | 1 0% | 0.5% | 1.0% |
| PEG-7 Glyceryl Cocoate | — | 0.3% | — | — | — | — | — | — | — | 0.5% |
| Trideceth-9 | — | 0.2% | — | — | 0.2% | — | — | — | — | — |
| Polysorbate 20 | — | — | 0.5% | — | — | — | — | — | 0.3% | 0.2% |
| PEG-40 Hydrogenated Castor Oil | — | — | 0.3% | — | 0.5% | — | — | — | 1.0% | — |
| PEG-6 Caprylic/Capric Glycerides | — | — | — | — | 0.3% | — | — | — | — | 0.2% |
| Polyglyceryl-4 Caprate | — | — | — | 2.0% | — | 0.5% | — | — | — | 0.5% |
| Polyquaternium-10 | — | 0.2% | — | 0.1% | — | — | — | 0.2% | 0.2% | — |
| Hydroxypropyl Guar Hydroxypropyltrimonium Chloride | 0.2% | — | 0.3% | 0.2% | 0.2% | 0.3% | 0.2% | 0.1% | — | — |
| Silicone Quaternium-22 | — | — | 0.3% | — | 0.3% | — | — | — | — | — |
| Dimethicone | — | 0.3% | — | — | — | — | — | — | 0.1% | — |
| Amodimethicone | — | 0.1% | — | 0.1% | 0.1% | — | — | — | 0.5% | — |
| *Argania Spinosa* Oil | — | — | 0.1% | 0.1% | 0.1% | — | 0.2% | — | — | — |
| Glycol Distearate | — | 0.5% | — | — | 0.5% | — | 0.3% | — | 0.5% | 0.5% |
| Isostearamide MIPA; Glyceryl Laurate | 1.0% | — | — | 1.5% | — | — | 0.3% | — | 1.0% | 0.5% |
| Sodium Chloride | 0.5% | 1.8% | 2.0% | 0.5% | 1.5% | 1.8% | 0.2% | 1.0% | — | 0.5% |
| PEG-120 Methyl Glucose Dioleate | 0.3% | 2.5% | 1.0% | — | 1.2% | — | — | — | 0.5% | — |
| Xanthan Gum | — | — | 0.5% | 0.6% | — | 0.7% | 2.0% | 1.0% | — | — |
| Cellulose | — | — | — | 0.1% | — | 0.1% | 0.1% | 0.2% | 0.1% | — |
| Zinc Pyrithione | — | 0.1% | — | — | — | — | — | — | 0.1% | — |
| Benzophenone-4 | — | 0.1% | 0.1% | 0.1% | 0.1% | — | 0.1% | — | 0.1% | — |
| Tetrasodium EDTA | 0.1% | — | — | 0.1% | 0.1% | — | 0.1% | — | 0.1% | — |
| Caffeine | — | 0.1% | 0.1% | — | — | 0.1% | — | — | 0.1% | — |
| Coumarin | — | 0.1% | 0.1% | — | 0.1% | 0.1% | 0.2% | 0.1% | 0.1% | — |
| Panthenol | 0.1% | 0.1% | 0.1% | 0.1% | 0.1% | 0.1% | — | 0.1% | 0.1% | 0.1% |
| Isopropyl Myristate | — | — | — | 0.3% | — | 0.1% | — | — | — | 0.2% |
| Linalool | — | — | 0.1% | 0.1% | — | 0.1% | 0.1% | — | 0.1% | — |
| *Citrus Limon* (Lemon) Peel Oil | 0.1% | — | 0.1% | — | — | 0.3% | — | 0.2% | 0.1% | 0.2% |
| Orange Oil | — | 0.2% | — | — | 0.2% | — | — | 0.2% | — | — |
| Limonene | — | 0.1% | — | — | — | — | 0.1% | — | 0.1% | — |
| Citric Acid | | | | | to pH 5.5 | | | | | |
| Perfumes, Dyes, Preservatives | | | | | q.s. | | | | | |

TABLE 47

Further formulation examples

| | 47a | 47b | 47c | 47d | 47e | 47f | 47g | 47h | 47i | 47j |
|---|---|---|---|---|---|---|---|---|---|---|
| Water | to 100% | | | | | | | | | |
| Product Example 2 | 7.0% | 3.0% | 2.0% | 4.0% | 4.0% | 2.5% | 4.0% | 3.5% | 3.0% | 3.0% |
| Sodium Lauryl Sulfate | — | 8.0% | 9.5% | — | — | — | — | 3.5% | — | — |
| Coco-Betaine | — | 5.0% | — | 5.5% | — | — | — | 3.0% | — | — |
| Cocamidopropyl Betaine | — | — | 3.0% | — | 5.0% | — | — | — | 3.0% | 2.0% |
| Sodium Cocoamphoacetate | — | — | 2.5% | 3.0% | — | 5.0% | — | 3.0% | 4.0% | — |

TABLE 47-continued

Further formulation examples

| | 47a | 47b | 47c | 47d | 47e | 47f | 47g | 47h | 47i | 47j |
|---|---|---|---|---|---|---|---|---|---|---|
| Disodium Lauryl Sulfosuccinate | — | — | 1.0% | — | — | — | — | 1.2% | — | — |
| Coco-Glucoside | — | — | — | 3.0% | 5.0% | 4.0% | 5.0% | 1.0% | — | 2.0% |
| Sodium Cocoyl Glutamate | — | — | — | 2.5% | — | 3.0% | 4.5% | 0.5% | 2.5% | 0.3% |
| Sodium Cocoyl Glycinate | — | — | — | — | 5.0% | — | 3.5% | — | 2.0% | 7.0% |
| Sodium Lauroyl Methyl Isethionate | — | — | — | 1.0% | — | 1.5% | — | 1.0% | 0.5% | 0.5% |
| Stearic Acid | — | — | 0.2% | — | — | — | — | 0.1% | — | 0.5% |
| Sucrose Cocoate | 0.5% | 0.4% | — | 1.0% | — | 0.2% | 0.2% | 0.3% | 1.0% | 0.3% |
| Glycerol | 1.5% | 0.3% | 0.5% | 0.5% | 0.8% | 0.5% | 1.0% | 0.5% | 0.5% | 1.0% |
| PEG-40 Hydrogenated Castor Oil | — | 1.0% | — | — | — | — | — | 0.3% | — | — |
| Polyglyceryl-4 Caprate | 1.0% | — | — | 0.5% | — | 2.5% | — | — | 0.9% | — |
| Polyquaternium-11 | — | 0.2% | — | — | 0.1% | — | — | 0.2% | — | 0.3% |
| Guar Hydroxypropyltrimonium Chloride | — | — | 0.3% | 0.2% | 0.2% | 0.3% | 0.2% | 0.1% | 0.2% | — |
| Dimethicone | — | 0.3% | — | — | — | — | — | 0.2% | — | — |
| Aminopropyl Dimethicone | — | 0.3% | 0.5% | — | — | — | — | 0.3% | — | — |
| *Helianthus Annuus* Seed Oil | 0.1% | — | 0.1% | — | — | 0.1% | — | 0.2% | — | — |
| Dicaprylylether | 0.5% | 0.3% | — | — | — | 0.2% | 0.3% | 0.5% | — | — |
| Sodium Hydroxypropyl Starch Phosphate | 0.2% | — | — | — | — | 0.5% | — | — | — | 0.5% |
| Palmitamidopropyltrimonium Chloride | — | — | 0.5% | — | — | — | — | 0.5% | 0.4% | — |
| Bis-(Isostearoyl/Oleoyl Isopropyl) Dimonium Methosulfate | 0.5% | 0.3% | — | — | — | — | 0.5% | — | — | — |
| Glycol Distearate | 0.2% | 0.1% | 0.2% | — | 0.4% | — | — | — | 0.5% | 0.2% |
| PEG-3 Distearate | — | 0.5% | — | — | — | — | — | 0.5% | — | — |
| Acrylates/C10-30 Alkyl Acrylate Crosspolymer | 0.5% | — | 0.4% | — | 0.5% | — | — | — | 0.5% | — |
| Sodium Hydroxide, 25% | 0.6% | — | 0.6% | — | 0.8% | — | — | — | 0.7% | — |
| Cocamide MEA | — | 0.8% | 1.0% | 1.0% | — | 0.4% | 0.6% | 1.0% | — | 0.3% |
| Sodium Chloride | 0.3% | 0.8% | 0.5% | — | 0.5% | 0.5% | — | 1.0% | 0.5% | 1.0% |
| Propylene Glycol; PEG-55 Propylene Glycol Oleate | — | 2.5% | — | — | — | — | — | 0.8% | — | — |
| Xanthan Gum | 0.2% | — | 0.2% | 1.2% | 0.5% | — | 1.5% | 0.2% | 1.0% | 0.9% |
| Algin | — | — | — | — | 0.7% | 1.2% | — | — | 0.5% | — |
| Benzophenone-4 | — | 0.1% | 0.2% | — | — | — | — | 0.2% | — | 0.1% |
| Menthol | 0.1% | — | 0.1% | — | — | — | — | 0.1% | 0.1% | 0.1% |
| Caffeine | — | 0.1% | 0.1% | 0.1% | 0.1% | — | — | 0.1% | — | 0.1% |
| Benzyl Alcohol | 0.1% | — | — | — | 0.1% | 0.1% | — | 0.1% | — | — |
| Hydrolyzed Wheat Protein | — | — | 0.1% | 0.1% | 0.1% | 0.2% | 0.2% | 0.1% | — | — |
| Octopirox | 0.2% | — | — | — | — | 0.1% | — | — | — | — |
| Salicylic acid | 0.1% | — | — | — | 0.1% | 0.1% | — | — | 0.1% | — |
| 1,2-Hexanediol | — | — | — | 0.2% | — | 0.5% | 0.5% | 0.2% | — | — |
| Isopropyl Myristate | — | 0.3% | — | 0.2% | — | — | — | 0.5% | 0.3% | — |
| Linalool | — | 0.1% | 0.1% | 0.1% | — | 0.1% | 0.1% | 0.1% | 0.1% | — |
| *Citrus Limon* (Lemon) Peel Oil | 0.1% | — | 0.1% | 0.3% | — | 0.2% | — | 0.1% | 0.1% | 0.2% |
| Orange Oil | — | 0.2% | — | 0.1% | 0.5% | — | — | — | — | — |
| Panthenol | 0.1% | 0.1% | — | 0.1% | 0.1% | 0.1% | 0.1% | 0.1% | 0.1% | 0.1% |
| Citric Acid | | | | | to pH 5.2 | | | | | |
| Perfumes, Dyes, Preservatives | | | | | q.s. | | | | | |

TABLE 48

List of raw materials used

| INCI | Trade name, company |
|---|---|
| 1,2-Hexanediol | Hydrolite-6 841129, Symrise |
| Acrylates/Beheneth-25 Methacrylate Copolymer | Novethix L-10 Polymer, Lubrizol |
| Acrylates/C10-30 Alkyl Acrylate Crosspolymer | TEGO Carbomer 841 SER, Evonik Nutrition & Care GmbH, 100% |
| Algin | Hydagen 558 P, BASF |
| Allantoin | Allantoin, DSM Nutritional Products, Inc. |
| *Aloe Barbadensis* Leaf Juice | Aloe-Con UP 40, Florida Food Products Inc. |
| alpha-Isomethyl Ionone | alpha-Isomethylionone, Chemos GmbH |

TABLE 48-continued

List of raw materials used

| INCI | Trade name, company |
|---|---|
| Alumina | Aeroxide Alu C, Evonik Nutrition & Care GmbH |
| Aluminum Chlorohydrate | Locron L, Clariant |
| Ammonium Lauryl Sulfate | Empicol AL 70, Albright & Wilson UK Limited |
| Aminopropyl Dimethicone | ABIL Soft AF 200, Evonik Nutrition & Care GmbH |
| Amodimethicone | DC 949, Dow Corning, 100% |
| *Argania Spinosa* Oil (*Argania Spinosa* Kernel Oil) | Argan Oil, DSM Nutritional Products Ltd. |
| Benzophenone-4 | Uvinul MS 40, BASF Corporation |
| Benzoic Acid | OriStar BZA, Orient Stars LLC |
| Benzyl Alcohol | Microcare BNA, THOR PERSONAL CARE SAS |
| Benzyl Salicylate | Seridefrizz Intense, Cheemyunion Quimica Ltda. |
| Bis-(Isostearoyl/Oleoyl Isopropyl) Dimonium Methosulfate | VARISOFT EQ 100, Evonik Nutrition & Care GmbH, 100% |
| Butylene Glycol | Butylene Glycol, Oxea Corparation |
| *Butyrospermum Parkii* Butter Extract | Cosmosil 600, International Cosmetic Science Centre |
| Caffeine | Caffeine, Merck KGaA/EMD Chemicals, Inc. |
| *Camellia Oleifera* Seed Oil | *Camellia Sasanqua* Oil, Ikeda Corporation |
| Caprylyl Glycol | Sensiva SC 10, Schülke& Mayr GmbH |
| Caprylyl/Capryl Glucoside | |
| Capryl/Capramidopropyl Betaine | TEGO Betaine 810, Evonik Nutrition & Care GmbH, 38% |
| Caprylic/Capric Triglyceride | TEGOSOFT CT, Evonik Nutrition & Care GmbH, 100% |
| Carbomer | TEGO Carbomer 140, Evonik Nutrition & Care GmbH, 100% |
| Cellulose | Arbocel A300, J. Rettenmaier & Sohne |
| Cetyl Ricinoleate | TEGOSOFT CR, Evonik Nutrition & Care GmbH, 100% |
| Cetrimonium Bromide | Rhodaquat M-242B/99, Rhodia |
| *Chamomilla Recutita* (Matricaria) Extract | Recentia CR, AkzoNobel Global Personal Care |
| Citral | Citral FF, Symrise AG |
| Citric Acid | Citric Acid USP Granular, DSM Nutritional Products, Inc. |
| *Citrus Aurantifolia* (Lime) Oil | AEC Lime Oil, A & E Connock, Perfumery & Cosmetics Ltd. |
| Cocamide DEA | REWOMID DC 212 S, Evonik Nutrition & Care GmbH, 100% |
| Cocamide MEA | REWOMID D 212, Evonik Nutrition & Care GmbH, 100% |
| Cocamidopropyl Betaine | TEGO Betain F 50, Evonik Nutrition & Care GmbH, 38% |
| Coco-Glucoside | Plantacare 818 UP, BASF Cognis, 51%, |
| Coco-Betaine | Dehyton AB 30, BASF Cognis, 31% |
| Coumarin | Rhodiascent extra pure, Rhodia Organics |
| *Curcuma Longa* (Turmeric) Root Extract | TEGO Turmerone, Evonik Nutrition & Care GmbH |
| Decyl Glucoside | Plantacare 2000 UP, BASF Cognis |
| Decyl Oleate | TEGOSOFT DO, Evonik Nutrition & Care GmbH, 100% |
| Dicaprylyl Ether | Cetiol OE, BASF Cognis |
| Dehydroacetic Acid | Unisept DHA (Universal Preserv-A-Chem, Inc.) |
| Dimethicone | DC 200 Fluid 100 cSt, Dow Corning, 100% |
| Disodium Cocoamphodiacetate | Rewoteric AM 2 C NM, Evonik Nutrition & Care GmbH |
| Disodium Cocoyl Glutamate | Planatpon ACG LC, BASF Cognis |
| Disodium EDTA | Dissolvine NA-2-P, AkzoNobel Global Personal Care |
| Disodium Lauryl Sulfosuccinate | REWOPOL SB F 12 P, Evonik Nutrition & Care GmbH, 95% |
| Distearyl Ether | Cosmacol SE, Sasol Germany GmbH |
| Ethylhexylglycerin | Sensiva SC 50, Schuelke & Mayr GmbH |
| Ethylhexyl Stearate; Phenoxyethanol; Polyglyceryl-4 Laurate; Sorbitan Laurate; Dilauryl Citrate | TEGO Wipe Flex, Evonik Nutrition & Care GmbH |
| Geraniol | Nerol 800, International Flavors & Fragrances Inc. |

TABLE 48-continued

List of raw materials used

| INCI | Trade name, company |
|---|---|
| Glucose | Organic Biovert Substrate, Lonza |
| Glycerol | Glycerol EP, vegetable, Spiga Nord, 99.7% |
| Glyceryl Caprylate | Dermosoft GMCY, Dr. Straetmans |
| Glyceryl Isostearate | Peceol Isostearique, Gattefosse |
| Glyceryl Oleate | TEGIN O V, Evonik Nutrition & Care GmbH |
| *Glycine Soya* (Soybean) Oil | Cropure Soybean, Croda Europe, Ltd. |
| Glycol Distearate | TEGIN G 1100 Pellets, Evonik Nutrition & Care GmbH, 100% |
| Guar Hydroxypropyltrimonium Chloride | Cosmedia Guar C 261, BASF Personal Care and Nutrition Gmbh/Jaguar C-17, Rhodia Inc. et al |
| *Helianthus Annuus* (Sunflower) Seed Oil | AEC Sunflower Oil, A & E Connock, Perfumery & Cosmetics Ltd. |
| Hydrolyzed Silk | Crosilk 10000, Croda Inc. |
| Hydrolyzed Wheat Protein | Gluadin WLM, BASF Cognis |
| Hydrolyzed Wheat Starch | Cropeptide W, Croda, Inc. |
| Hydroxyethyl Ethylcellulose | Structure Cel 4400 E, AkzoNobel Global Personal Care |
| Hydroxypropyl Guar Hydroxypropyltrimonium Chloride | Jaguar C-162, Rhodia, 100% |
| Hydroxypropyl Methylcellulose | TEGOCEL HPM 50, Evonik Nutrition & Care GmbH, 100% |
| Isoceteth-20 | TEGO Alkanol IC 20, Evonik Nutrition & Care GmbH, 100% |
| Isopropyl Myristate | TEGOSOFT M, Evonik Nutrition & Care GmbH, 100% |
| Isopropyl Palmitate | TEGOSOFT P, Evonik Nutrition & Care GmbH, 100% |
| Isostearamide MIPA; Glyceryl Laurate | ANTIL SPA 80, Evonik Nutrition & Care GmbH, 100% |
| Lactic Acid | AEC Lactic Acid, A & E Connock, Perfumery & Cosmetics Ltd. |
| Lactis Proteinum | AEC Whey Protein, A & E Connock, Perfumery & Cosmetics Ltd. |
| Laureth-5 Carboxylic Acid | Marlowet 1072, Sasol Germany GmbH - Marl |
| Lauric Acid | Prifrac 2920, Croda Europe, Ltd. |
| Lauryl Glucoside | Plantacare 1200 UP, BASF Cognis, 50% |
| *Lavandula Angustifolia* (Lavender) Oil | AEC Lavender Oil, A&E Connock Ltd. |
| Lecithin | AEC Lecithin Powder, A & E Connock, Perfumery & Cosmetics Ltd. |
| Limonene | Dipentene No. 122, Hercules Inc. |
| *Citrus Limon* (Lemon) Peel Oil | Fragrance Resources |
| *Cymbopogon Schoenanthus* (Lemongrass) Oil | AEC Lemongrass Oil, A&E Connock Ltd. |
| Linalool | Lipofresh, Lipo Chemicals, Inc. |
| Magnesium Chloride | OriStar MCL, Orient Stars LLC |
| Maltodextrin | Farmal MD 10, Corn Products International |
| *Malva Sylvestris* (Mallow) Leaf Extract | Herbasec Mallow Leaves, Cosmetochem International AG |
| *Mangifera Indica* (Mango) Fruit Extract | Mango Extract, Draco Natural Products |
| Menthol | OriStar MC, Orient Stars LLC |
| Methylisothiazolinone | Microcare MT, Thor Specialties, Inc. |
| *Mentha Piperita* (Peppermint) Oil | AEC Peppermint Oil, A&E Connock Ltd. |
| MIPA-Laureth Sulfate | Zetesol 2056, Zschimmer & Schwarz GmbH |
| Octopirox | Octopirox, Clariant Intl. Ltd. |
| *Olea Europaea* (Olive) Fruit Oil | Cropure Olive, Croda Europe, Ltd. |
| Orange Oil | Fragrance Resources |
| Palmitamidopropyltrimonium Chloride | VARISOFT PATC, Evonik Nutrition & Care GmbH, 60% |
| Panthenol | D-Panthenol USP, BASF, 100% |
| PEG-120 Methyl Glucose Dioleate | ANTIL 120 Plus, Evonik Nutrition & Care GmbH, 100% |
| PEG-150 Distearate | REWOPAL PEG 6000 DS A, Evonik Nutrition & Care GmbH, 100% |
| PEG-18 Castor Oil Dioleate | Marlowet CG, Sasol Germany GmbH |
| PEG-18 Glyceryl Oleate/Cocoate | ANTIL 171, Evonik Nutrition & Care GmbH, 100% |

TABLE 48-continued

List of raw materials used

| INCI | Trade name, company |
|---|---|
| PEG-200 Hydrogenated Glyceryl Palmate; PEG-7 Glyceryl Cocoate | REWODERM LI S 80, Evonik Nutrition & Care GmbH, 100% |
| PEG-3 Distearate | TEGIN D 1102, Evonik Nutrition & Care GmbH, 100%; Cutina TS, BASF Cognis, 100% |
| PEG-40 Hydrogenated Castor Oil | TAGAT CH 40, Evonik Nutrition & Care GmbH, 100% |
| PEG-6 Caprylic/Capric Glycerides | TEGOSOFT GMC-6, Evonik Nutrition & Care GmbH, 100% |
| PEG-7 Glyceryl Cocoate | TEGOSOFT GC, Evonik Nutrition & Care GmbH, 100% |
| Perfume Pink Grapefruit | Fragrance Resources |
| Perfume Spicy Herbs | Fragrance Resources |
| *Persea Gratissima* (Avocado) Oil | Cropure Avocado, Croda Europe, Ltd. |
| Petrolatum | Merkur 115, Sasol Wax GmbH |
| Phenethyl Alcohol | Etaphen, Vevy Europe SpA |
| Phenoxyethanol | S&M Phenoxyethanol, Schulke & Mayr GmbH |
| Phenoxyethanol; Ethylhexylglycerol | Euxyl PE 9010, Schulke & Mayr GmbH |
| Phenoxyethanol; Methylparaben; Ethylparaben; Butylparaben; Propylparaben; Isobutylparaben | Euxyl K 300, Schuelke & Mayr GmbH |
| Polyaminopropyl Biguanide | Microcare MBG, Thor |
| Polyglyceryl-3 Palmitate | Dermofeel PP, Dr. Straetmans |
| Polyglyceryl-4 Caprate | TEGOSOFT PC 41, Evonik Nutrition & Care GmbH, 100% |
| Polyglyceryl-6 Caprylate; Polyglyceryl-3 Cocoate; Polyglyceryl-4 Caprate; Polyglyceryl-6 Ricinoleate | TEGO Solve 61, Evonik Nutrition & Care GmbH, |
| Polyquaternium-10 | Polymer JR 400, Amerchol, 100% |
| Polyquaternium-11 | Dehyquart CC 11, BASF Personal Care and Nutrition Gmbh/Luviquat PQ 11 PN, BASF Corporation |
| Polyquaternium-7 | Merquat 550, Nalco, 100% |
| Polysorbate 20 | TEGO SML 20, Evonik Nutrition & Care GmbH, 100% |
| Potassium Sorbate | Euxyl K 712, Schülke & Mayr GmbH |
| Propylene Glycol | Euxyl K 320, Schülke & Mayr GmbH |
| Propylene Glycol; PEG-55 Propylene Glycol Oleate | ANTIL 141 Liquid, Evonik Nutrition & Care GmbH |
| *Prunus Amygdalus* Dulcis (Sweet Almond) Oil | Cropure Almond, Croda Europe, Ltd. |
| *Prunus Cerasus* (Bitter Cherry) Fruit Extract | *Prunus Cerasus* Fruit, Kirschen Extract, Botanica GmbH |
| *Ricinus Communis* Seed Oil | Lipovol CO, Lipo Chemicals |
| Rosemary Oil | Fragrance Resources |
| *Salvia Officinalis* (Sage) Oil | AEC Sage Oil, A&E Connock Ltd. |
| Salicylic Acid | OriStar SCA, Orient Stars LLC |
| Silica | Aerosil 130, Evonik Degussa GmbH |
| Silicone Quaternium-22 | ABIL T Quat 60, Evonik Nutrition & Care GmbH, 65% |
| Silicone Quaternium-22; Polyglycerol-3 Caprate; Dipropylene Glycol; Cocamidopropyl Betaine | ABIL ME 45, Evonik Nutrition & Care GmbH, 30% |
| *Simmondsia Chinensis* (Jojoba) Seed Oil | AEC *Jojoba* Oil Refined, A & E Connock, Perfumery & Cosmetics Ltd. |
| Sodium Benzoate | Euxyl K 712, Schülke & Mayr GmbH |
| Sodium Cetearyl Sulfate | Lanette E, BASF Personal Care and Nutrition GmbH |
| Sodium Cocoamphoacetate | REWOTERIC AM C, Evonik Nutrition & Care GmbH, 32% |
| Sodium Cocoamphopropionate | REWOTERIC AM KSF 40, Evonik Nutrition & Care GmbH, 40% |
| Sodium Coco-Sulfate | Texapon HC G, BASF |
| Sodium Cocoyl Glutamate | Plantapon ACG HC, BASF Cognis |
| Sodium Cocoyl Glycinate | Hostapon SG, Clariant; Amilite GCS-11, Ajinomoto |
| Sodium/Disodium Cocoyl Glutamate | PERLASTAN SC 25 NKW, Schill&Seilacher, 25%, |
| Sodium Hydroxide | Unichem SOHYD, Universal Preserv-A-Chem, Inc. |
| Sodium Hydroxypropyl Starch Phosphate | Pure-Gel, Grain Processing Corporation |
| Sodium Isethionate | Hostapon SI, Company Clariant International Ltd |
| Sodium Lactate | Sodium Lactate Solution About 50%, Merck KGaA/EMD Chemicals, Inc. |

TABLE 48-continued

List of raw materials used

| INCI | Trade name, company |
|---|---|
| Sodium Lactate; Sodium PCA; Glycine; Fructose; Urea; Niacinamide; Inositol; Sodium Benzoate; Lactic Acid | LACTIL, Evonik Nutrition & Care GmbH |
| Sodium Laureth Sulfate | Texapon NSO, BASF Cognis, 28% |
| Sodium Lauroamphoacetate | ColaTeric SLAA, Colonial Chemical Inc |
| Sodium Lauroyl Isethionate | Yongan SLI, Huanggang Yongan Pharmaceutical Co., Ltd |
| Sodium Lauroyl Methyl Isethionate | Iselux, Innospec Active Chemicals |
| Sodium Lauryl Sulfate | Texapon LS 35, BASF Cognis, 30% |
| Sodium Trideceth Sulfate | Rhodapex EST-30, Rhodia |
| Sorbitan Caprylate | Sorbon S-10, Toho Chemical Industry Co., Ltd. |
| Stearic Acid | Pristerene 4922, Croda Europe, Ltd. |
| Stearyl Alcohol | TEGO Alkanol 18, Evonik Nutrition & Care GmbH |
| Styrene/Acrylates Copolymer | Acudyne HS, The Dow Chemical Company |
| Sucrose Cocoate | TEGOSOFT LSE 65 K, Evonik Nutrition & Care GmbH, 100% |
| Tetrasodium EDTA | Versene 100, The Dow Chemical Company |
| Tocopherol | Euxyl K 700, Schülke & Mayr GmbH |
| Trideceth-9 | Marlipal O 13/90, Sasol Germany GmbH - Marl |
| *Triticum Vulgare* Germ Oil | Cropure Wheatgerm, Croda Europe, Ltd. |
| Xanthan Gum | Keltrol CG-SFT, CP Kelco, 100% |
| Zinc Pyrithione | Microcare ZP, THOR PERSONAL CARE SAS |

The invention claimed is:

1. A polyglycerol partial ester obtainable by esterification of a polyglycerol with a carboxylic acid mixture comprising:
    a) at least one short-chain dicarboxylic acid having 2 to 12 carbon atoms, and
    b) at least one saturated fatty acid having 6 to 14 carbon atoms, wherein the molar ratio of polyglycerol to dicarboxylic acid to saturated fatty acid is in a ratio of from 3.1:1.0:0.5 to 14:1.0:6.0.

2. The polyglycerol partial ester according to claim 1, wherein the polyglycerol has an average degree of condensation N of 1.5 to 9.

3. The polyglycerol partial ester according to claim 1, wherein the polyglycerol used has a hydroxyl number of 1500 to 900 mg KOH/g.

4. The polyglycerol partial ester according to claim 1, wherein the short-chain dicarboxylic acid is selected from aliphatic, linear dicarboxylic acids, in particular oxalic acid, malonic acid, succinic acid, glutaric acid, adipic acid, pimelic acid, suberic acid, azelaic acid, sebacic acid, and dodecanedioic acid.

5. The polyglycerol partial ester according to claim 1, wherein the saturated fatty acid is selected from unbranched, unsubstituted fatty acids.

6. The polyglycerol partial ester according to claim 1, wherein the esterification the molar ratio of a) to b) is from 1.0:0.7 to 1.0:3.0.

7. The polyglycerol partial ester according to claim 1, wherein at 1 bar it has a turbidity point of 45 to 75° C.

8. The polyglycerol partial ester according to claim 1, wherein it has an HLB value of 13 to 17.

9. The polyglycerol partial ester according to claim 1, wherein it has a surface tension of less than 28 mN/m in 1.0% aqueous solution at 20° C.

10. The polyglycerol partial ester according to claim 1, wherein it has a saponification number of 70 to 199 mg KOH/g.

11. The use of at least one polyglycerol partial ester according to claim 1 as solubilizer, particularly in cosmetic or pharmaceutical preparations.

* * * * *